(12) United States Patent
Okumura

(10) Patent No.: US 10,743,823 B2
(45) Date of Patent: Aug. 18, 2020

(54) X-RAY IMAGING APPARATUS

(71) Applicant: Shimadzu Corporation, Kyoto (JP)

(72) Inventor: Hiroshi Okumura, Kyoto (JP)

(73) Assignee: Shimadzu Corporation,
Nishinokyo-Kuwabaracho, Nakagyo-ku,
Kyoto-shi, Kyoto (JP)

( * ) Notice: Subject to any disclaimer, the term of this patent is extended or adjusted under 35 U.S.C. 154(b) by 131 days.

(21) Appl. No.: 15/983,351

(22) Filed: May 18, 2018

(65) Prior Publication Data
US 2019/0350541 A1   Nov. 21, 2019

(51) Int. Cl.
*A61B 6/08*  (2006.01)
*A61B 6/06*  (2006.01)
*H05B 45/37*  (2020.01)

(52) U.S. Cl.
CPC .................. *A61B 6/08* (2013.01); *A61B 6/06* (2013.01); *H05B 45/37* (2020.01)

(58) Field of Classification Search
CPC .......... A61B 6/06; A61B 6/08; H05B 33/0815
See application file for complete search history.

(56) References Cited

U.S. PATENT DOCUMENTS

2018/0249971 A1* 9/2018 Okumura ................. A61B 6/06
2018/0299099 A1* 10/2018 Yamaguchi ............ G21K 1/046

FOREIGN PATENT DOCUMENTS

| JP | 07-241286 A | 9/1995 | |
| JP | 2007-229387 A | 3/2006 | |
| JP | 3197796 U | 6/2015 | |
| WO | WO-2017046929 A1 * | 3/2017 | ............... A61B 6/06 |

OTHER PUBLICATIONS

Notification of Reasons for Refusal from JPO dated Nov. 9, 2018 in related application JP 2015-214231 (with machine translation).

* cited by examiner

*Primary Examiner* — Marcus H Taningco
(74) *Attorney, Agent, or Firm* — Muir Patent Law, PLLC

(57) ABSTRACT

Provided is an X-ray imaging apparatus equipped with an LED driver circuit capable of properly and safely lighting an LED lamp even when an LED driver circuit is connected to any one of a plurality of internal power supplies different in voltage in the case of using an LED lamp as a collimator lamp. The LED driver circuit is provided with a rectifier circuit, a smoothing circuit, an input voltage level detector, a power connection switching unit for switching a change-over switch, and a DC-DC converter circuit. The DC-DC converter circuit is composed of a current control type DC chopper circuit and configured to measure the current from the voltage of both ends of a resistor and perform ON/OFF control of a transistor on the basis of the current to thereby function as a step-up/down chopper circuit or step-down chopper circuit.

9 Claims, 5 Drawing Sheets

X-RAY IMAGING APPARATUS

TECHNICAL FIELD

The present invention relates to an X-ray imaging apparatus for performing X-ray imaging or X-ray fluoroscopy, wherein the X-ray imaging apparatus is equipped with an X-ray tube, an X-ray detector, a collimator provided with a plurality of collimator leaves for changing an X-ray radiation field irradiated from the X-ray tube toward a subject and a collimator lamp for making the X-ray radiation field to be adjusted by the collimator leaves visible, and a plurality of types of internal power supplies different in voltage from each other.

BACKGROUND ART

In such an X-ray imaging apparatus, when adjusting an X-ray radiation field which is a range of an X-ray irradiated from an X-ray tube to a subject using a collimator, the irradiation field of the X-ray to be adjusted by the collimator mechanism is confirmed by forming an irradiation field of visible light by turning on the collimator lamp arranged on a side opposite to the subject with respect to the collimator and visually recognizing the irradiation field of the visible light.

In such an X-ray imaging apparatus, it is preferable that the brightness of the light irradiation field by the collimator lamp be as bright as possible for positioning the imaging. However, particularly when imaging a head portion or a neck portion, the light irradiation field is positioned near the face of the subject, so when the operator turns on the collimator lamp, there is a disadvantage that the light directly enters the subject's eye, making the subject feel uncomfortable. Under the circumstance, Patent Document 1 discloses an X-ray imaging apparatus. In the imaging apparatus, when the lamp lighting switch is turned to light the collimator lamp, time measurement is started by a timer and it is judged whether or not head-and-neck imaging is performed based on portion information input from the outside. Only in the case of performing head-and-neck imaging, the lamp voltage setting signal to be output to the lamp power supply circuit is controlled so that the voltage applied to the collimator lamp gradually increases and reaches a predetermined value.

PRIOR ART

Patent Document

Patent Document 1: Japanese Patent Application Publication No. 2007-229387

SUMMARY OF THE INVENTION

Problems to be Solved by the Invention

As a collimator lamp described above, a halogen lamp has been conventionally used. However, in recent years, it has been studied to use an energy-saving and long-life LED lamp as a collimator lamp. At this time, as a power source for lighting a conventional halogen lamp, an AC 12 V (volt) power source is usually used. On the other hand, as a power source for lighting an LED lamp, a DC power supply is preferably used.

FIG. 5 is a circuit diagram showing a power supply system of a conventional general X-ray imaging apparatus.

In the conventional X-ray imaging apparatus, an AC 12 V collimator lamp power supply system for lighting the halogen lamp 27 as a collimator lamp in the collimator 26 and a DC 24 V mechanical load power supply system for driving a mechanical load 28, such as, e.g., a brake, a motor, a clutch, and a solenoid. In the AC 12 V collimator lamp power supply system, the AC 200 V commercial power supply 29 is converted into AC 100 V by the first transformer 21 and further converted into AC 12 V by the second transformer 22 to thereby obtain an internal power supply for the halogen lamp 27. On the other hand, in the DC 24 V mechanical load power supply system, the AC 200 V commercial power source 29 is kept as AC 200 V by the first transformer 21, and then converted into DC 24 V by the AC/DC converter 23 to thereby obtain an internal power supply for the mechanical load 28. Note that in FIG. 5, the reference numeral "24" denotes a switch for the collimator 26, and the reference numeral "25" denotes a switch for the mechanical load 28.

In such a conventional X-ray imaging apparatus, in cases where an LED lamp is used instead of a halogen lamp 27 as a collimator lamp, in order to change the collimator lamp of the already delivered and running X-ray imaging apparatus from the halogen lamp 27 to an LED lamp, it is preferable to replace only the parts inside the collimator because the work onsite is easy and most of the existing parts can be used, so the number of parts to be replaced is fewer and it is less expensive. In this case, an LED driver circuit capable of lighting the LED lamp with AC 12 V of the collimator lamp power supply system is required.

In such a conventional X-ray imaging apparatus, in cases where an LED lamp is used instead of the halogen lamp 27 as a collimator lamp, in the case of changing the collimator lamp of the X-ray imaging apparatus from the halogen lamp 27 to an LED lamp before the shipment from the factory, the second transformer 22 in FIG. 5 may be changed to the AC/DC converter. However, in order to configure the device at lower price, it is conceivable to light the LED lamp by using the DC 24 V mechanical load power supply system. In this case, an LED driver circuit capable of lighting the LED lamp with DC 24 V of the mechanical load power supply system for driving the mechanical load 28 is required.

On the other hand, in the case of using an LED lamp as a collimator lamp, the voltage required for driving the LED lamp is typically DC 13.8 V (maximum 16.0 V). In general, in the case of using an LED lamp as a collimator lamp, a white LED lamp is used in which a blue LED using a GaN (gallium nitride) semiconductor is covered by a yellow fluorescence substance. In order to obtain the brightness corresponding to the international standard and/or each country's standard in a limited space, a configuration in which four white LED lamps are arranged in a 2×2 matrix is adopted. These four LED lamps are generally connected in series for the purpose of, e.g., preventing an increase in the number of lines and doubling of current due to a parallel connection and occurrence of failure. In an LED using a GaN semiconductor, the forward voltage Vf is 3.45 V (maximum 4.00 V). Therefore, when four of these are arranged in series, the forward voltage necessary for lighting the LED lamp is DC 13.8 V.

In the case of an LED driver circuit capable of lighting the LED lamp with AC 12 V of the aforementioned collimator lamp power supply system, it is necessary to make DC 13.8 V from AC 12 V by a rectifying/smoothing circuit. In this case, unless the capacitance of the smoothing circuit capacitor is limited to a certain extent, the rush current for charging the capacitor when the power supply is turned on becomes excessive, resulting in a large circuit. Therefore, it is necessary to allow the ripple to some extent in the smoothed voltage waveform and suppress the capacitor capacity of the smoothing circuit to some extent. At this time, when a ripple of about 6 V is allowed for AC 12 V, the smoothed voltage becomes a fluctuating waveform of DC 11 V to DC 17 V, and therefore the moment when it becomes larger than the forward voltage of 13.8 V of the LED lamp and the moment when it becomes smaller than that coexist. For this reason, the LED driver circuit cannot always cope with step-up or step-down, and therefore a step-up/down mode circuit is required.

On the other hand, in the case of an LED driver circuit capable of lighting the LED lamp with DC 24 V of a mechanical load power supply system for driving the aforementioned mechanical load, a rectifying/smoothing circuit used in the case of a power supply system for a collimator lamp is unnecessary and the input voltage DC 24 V is larger than the forward voltage 13.8 V of the LED lamp. Therefore, a step-down mode circuit is required. It is not impossible to create 13.8 V which is a forward voltage of the LED lamp using a step-up/down mode circuit for the DC 24 V input. In this case, however, the ground potential reaches about 40 V. For this reason, it is necessary to improve the withstand voltage performance of the LED driver circuit, causing a problem that the circuit increases in size.

In this way, the LED driver circuit capable of lighting the LED lamp with AC 12V of a collimator lamp power supply system and the LED driver circuit capable of lighting the LED lamp with DC 24V of a mechanical load power supply system for driving a mechanical load become separate circuits. Therefore, at the time of the 12 V AC input and that of the DC 24 V input, it can be considered to adopt a method of preparing respective dedicated LED driver circuit boards and selectively using them and a method of mounting two types of driver circuits on a single LED driver circuit board and setting them according to the input voltage.

However, in the case of adopting the former method in which dedicated LED driver circuit boards are prepared and selectively used, it become impossible to standardize the substrate and therefore the cost increases, and if an erroneous board is connected due to mis-ordering or the like, there is a possibility that the equipment is damaged, or smoke or ignition occurs.

On the other hand, in the case of adopting the latter method in which two kinds of driver circuits are mounted on a single LED driver circuit board and are set depending on the input voltage, although it becomes possible to reduce the equipment cost by standardizing the substrate, there is a risk of misconfiguration, and also in this case, there is a possibility that the device is damaged or smoke or ignition occurs.

The present invention has been made to solve the aforementioned problems, and aims to provide an X-ray imaging apparatus equipped with an LED driver circuit capable of properly and safely lighting an LED lamp even when the LED driver circuit is connected to any one of a plurality of internal power supplies different in voltage in the case of using an LED lamp as a collimator lamp.

Means for Solving the Problems

According to the invention as recited in claim 1, an X-ray imaging apparatus includes: an X-ray tube; an X-ray detector configured to detect an X-ray irradiated from the X-ray tube and passed through an subject; a collimator equipped with a plurality of collimator leaves for changing an X-ray radiation field irradiated from the X-ray tube toward the subject and a collimator lamp for making the X-ray radiation field to be adjusted by the collimator leaves visible; and a plurality of types of internal power supplies different in voltage from each other. The collimator lamp includes an LED lamp, and an LED driver circuit is provided. Any one of the plurality of types of internal power supplies is connected to the LED lamp, the LED driver circuit is configured to convert a voltage of the connected internal power supply to a forward voltage of the LED lamp to thereby light the LED lamp.

According to an invention as recited in claim 2, in the invention as recited in claim 1, the LED driver circuit includes: a DC-DC converter circuit capable of switching between a step-up/down mode or a step-up mode and a step-down mode according to a connection mode connecting any one of the plurality of types of internal power supplies with the DC-DC converter circuit; input voltage level detection means; and connection switching means configured to switch the connection mode connecting any one of the plurality of types of internal power supplies with the DC-DC converter circuit based on an input voltage detected by the input voltage level detection means.

According to an invention as recited in claim 3, in the invention as recited in claim 2, the plurality of types of internal power supplies different in voltage include an internal power supply having a voltage higher than the forward voltage of the LED lamp and an internal power supply having a voltage lower than the forward voltage of the LED lamp.

According to an invention as recited in claim 4, in the invention as recited in claim 1, the LED driver circuit includes: a step-down circuit for stepping down a voltage of any one of the plurality of types of internal power supplies to a voltage equal to or lower than the forward voltage of the LED lamp; and a step-up circuit for stepping up the voltage stepped down by the step-down circuit to the forward voltage of the LED lamp.

According to an invention as recited in claim 5, in the invention as recited in claim 4, at least one of the plurality of types of internal power supplies different in voltage is an internal power supply having a voltage higher than the forward voltage of the LED lamp.

According to an invention as recited in claim 6, in the invention as recited in any one of claims 1 to 5, the plurality of types of internal power supplies different in voltage include an AC power supply having a voltage lower than the forward voltage of the LED lamp and a DC power supply having a voltage higher than the forward voltage of the LED lamp.

Effects of the Invention

According to the invention as recited in claim 1, in the case of using an LED lamp as a collimator lamp, even when the LED driver circuit is connected to any one of a plurality of internal power supplies different in voltage, it becomes possible to light the LED lamp properly and safely.

According to the invention as recited in claims 2 and 3, by selecting either the step-up/down mode or step-up mode or the step-down mode depending on an internal power supply to be connected, it is possible to light the LED lamp properly and safely.

According to the invention as described in claim 4 or 5, by lowering the voltage of the power supply to be connected to the forward voltage of the LED lamp or below and then increasing the voltage to the forward voltage, it is possible to light the LED lamp properly and safely.

According to the invention as recited in claim 6, for example, even in cases where the LED driver circuit is connected to either a conventional halogen lamp power source or a mechanical load power source, it is possible to light the LED lamp properly and safely.

EMBODIMENTS FOR CARRYING OUT THE INVENTION

Figure 1:
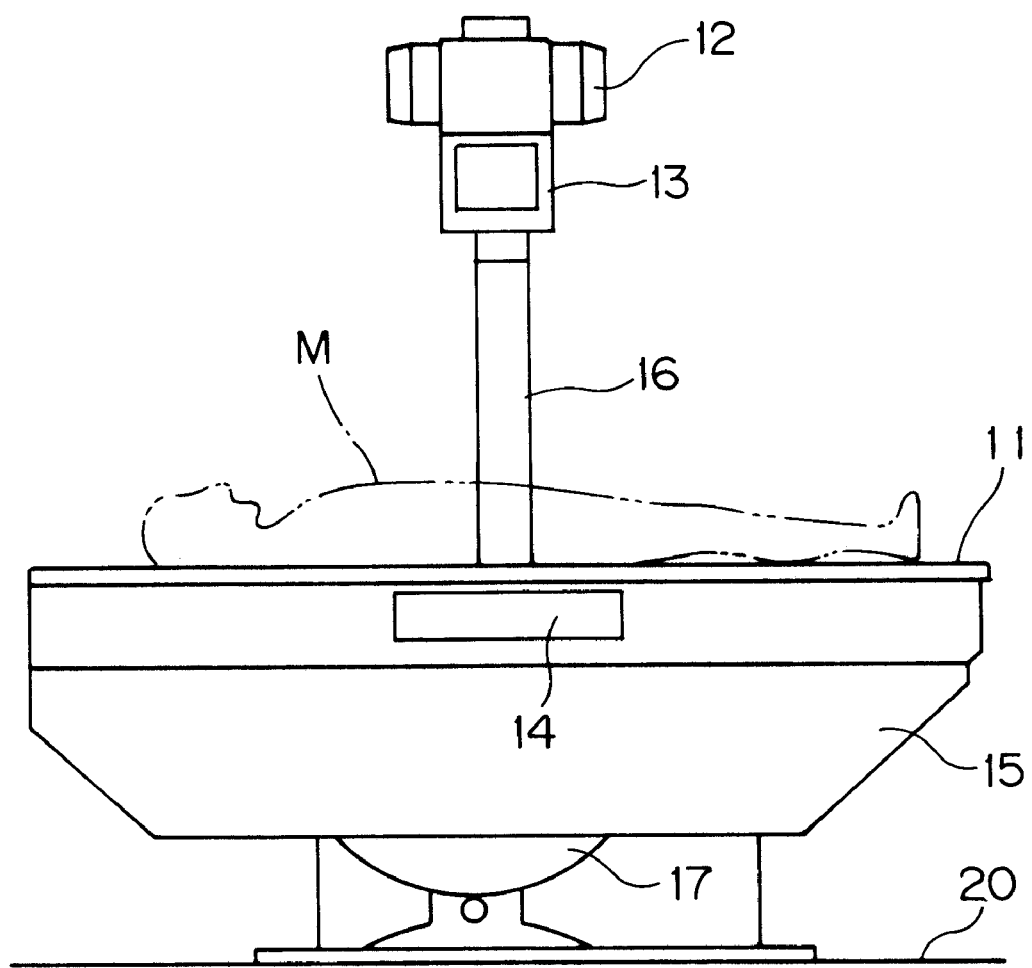
FIG. 1 is a schematic front view of a fluoroscopic imaging table as an X-ray imaging apparatus according to the present invention.

Hereinafter, embodiments of the present invention will be described with reference to the attached drawings. FIG. 1 is a schematic front view of a fluoroscopic imaging table as an X-ray imaging apparatus according to the present invention.

This X-ray fluoroscopic imaging table is provided with a top board 11 for placing a subject M, an X-ray tube 12 for irradiating an X-ray to the subject M on the top board 11, a collimator 13 for regulating the irradiation field of the X-ray irradiated from the X-ray tube 12, an X-ray detector 14, such as, e.g., an image intensifier (I.I.) and a flat panel detector, for detecting the X-ray irradiated from the X-ray tube 12 and passed through subject M. The X-ray tube 12 and the collimator 13 are supported by a support post 16 connected to a body 15. Also, the top board 11 is connected to the body 15 by a coupling mechanism (not shown).

The support post 16 is configured to be movable in the horizontal direction with respect to the body 15. Along with the movement of the support post 16, the X-ray tube 12 and the collimator 13 are also reciprocally moved along the surface of the top board 11. The body 15 is disposed rotatably with respect to the leg portion 17. For this reason, as shown in FIG. 1, the top board 11 can take a recumbent imaging posture in which the surface of the top board 11 is parallel to the floor surface 20 and extends in the horizontal direction and a standing imaging posture in which the surface of the top board 11 is orthogonal to the floor surface 20 and extends in the vertical direction.

Figure 2:
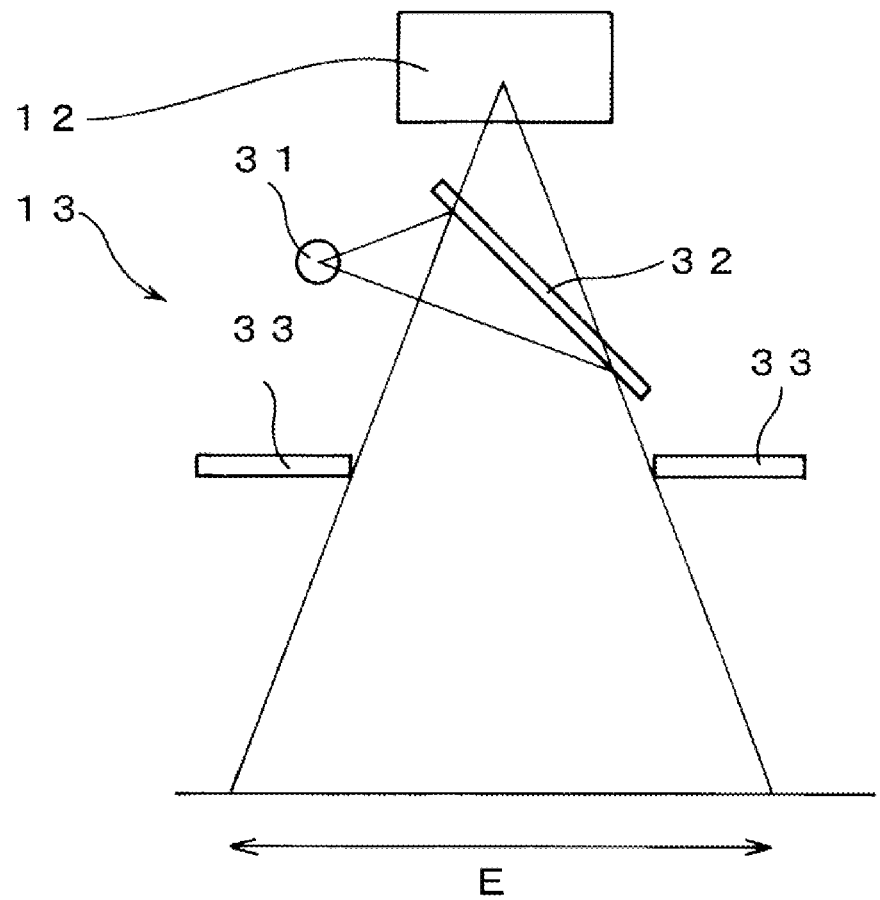
FIG. 2 is a schematic diagram showing a collimator 13 together with an X-ray tube 12.

FIG. 2 is a schematic diagram showing the aforementioned collimator 13 together with the X-ray tube 12.

This collimator 13 is equipped with four collimator leaves 33 for limiting the radiation field of the X-ray irradiated from the X-ray tube 12. In this figure, only two collimator leaves 33 are illustrated, but in reality, a rectangular X-ray radiation field is formed by four collimator leaves 33. In this figure, the X-ray irradiation field is indicated by the reference symbol E. Further, the collimator 13 is equipped with an LED lamp 31 as a collimator lamp for irradiating visible light so as to make the X-ray irradiation field visible. The visible light emitted from the LED lamp 31 is reflected by the mirror 32 in the direction of the collimator leaf 33, so that a rectangular visible light irradiation field is formed by the four collimator leaves 33. The focal point of the X-ray tube 12 and that of the LED lamp 31 are arranged at a conjugate position, so that the size of the irradiation field of the visible light becomes the same as the size of the X-ray irradiation field.

Figure 3:
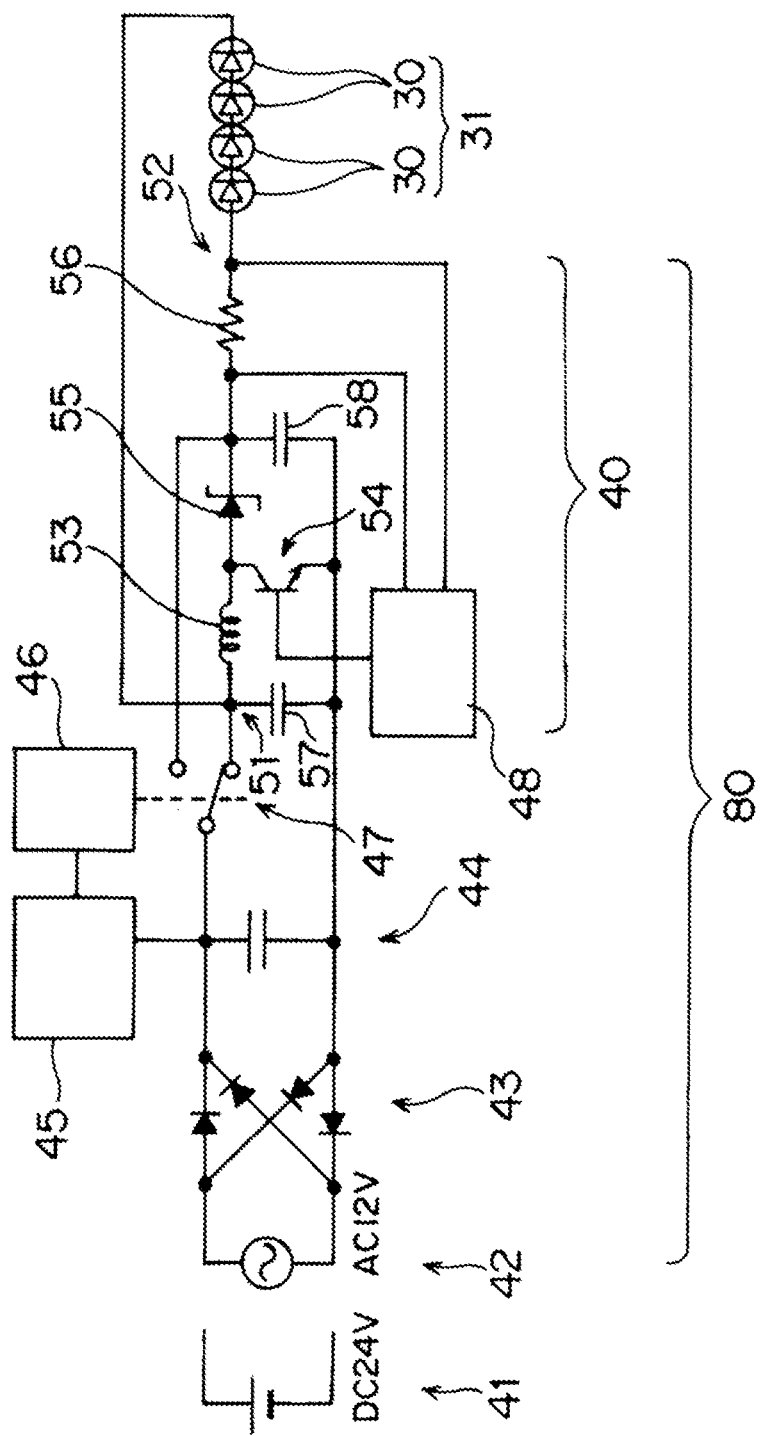
FIG. 3 is a circuit diagram of an LED driver circuit 80 according to a first embodiment of the present invention.

Next, the configuration of the LED driver circuit 80 which is a characteristic part of the present invention will be described. FIG. 3 is a circuit diagram of an LED driver circuit 80 according to a first embodiment of the present invention.

Figure 5:
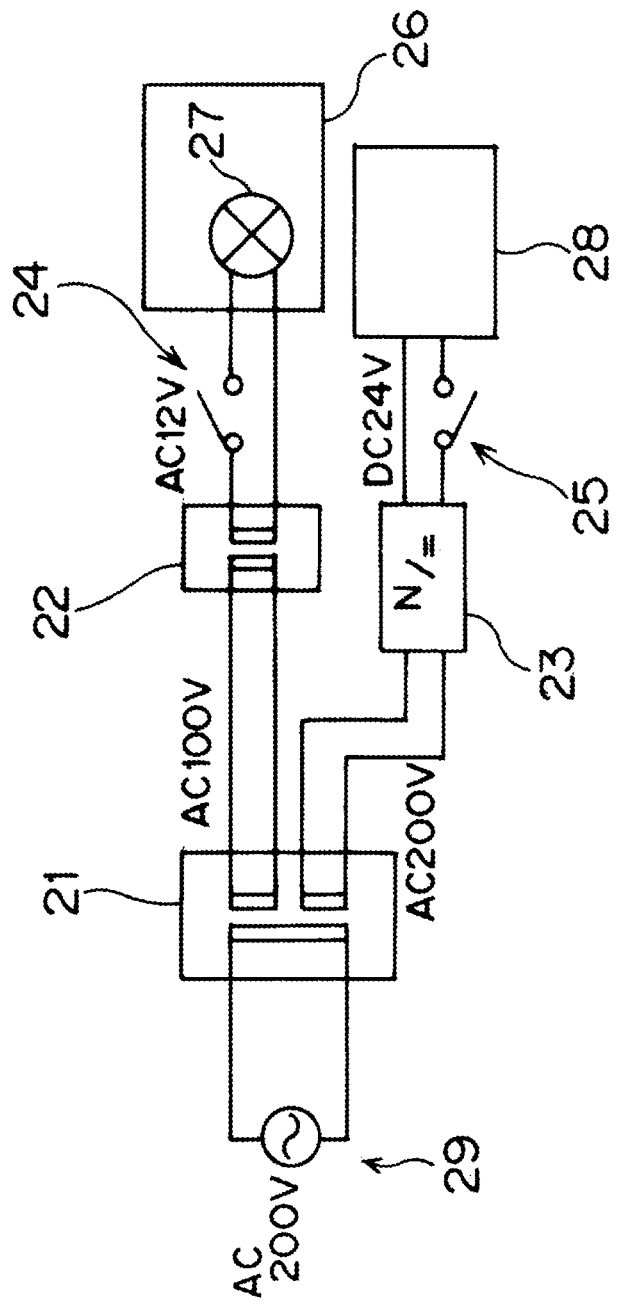
FIG. 5 is a circuit diagram showing a power supply system of a conventional general X-ray imaging apparatus.

This LED driver circuit 80 is for supplying a forward voltage of each LED 30 to the LED lamp 31 by selectively connecting the DC 24 V internal power supply 41 and the AC 12 V internal power supply 42 produced by the first transformer 21, the second transformer 22, and the AC/DC converter 23 shown in FIG. 5 to the LED lamp 31 composed of four LEDs 30 connected in series. As described above, the forward voltage of the LED lamp 31 composed of four LEDs 30 is DC 13.8 V.

The LED driver circuit 80 according to this first embodiment is provided with a rectifier circuit 43 equipped with four diodes, a smoothing circuit 44 equipped with a capacitor, an input voltage level detector 45, a power connection switching unit 46 for switching a change-over switch 47, and a DC-DC converter circuit 40.

The aforementioned input voltage level detector 45 is composed of, for example, a comparator circuit for comparing a reference supply voltage with an input supply voltage. Here, the reference supply voltage is set to, for example, 20 V. Further, the power connection switching unit 46 is composed of a c-contact relay which operates in conjunction with the output of the input voltage level detector 45.

The DC-DC converter circuit 40 is composed of a current control type DC chopper circuit including a pair of capacitors 57 and 58, a coil 53, a Schottky barrier diode 55, a transistor 54, a resistor 56, and a DC chopper controller 48. In the DC-DC converter circuit 40, a current is measured from the voltage across the resistor 56, and ON/OFF of the transistor 54 is controlled based on the current.

In the case in which the AC 12V internal power supply 42 is connected as the internal power supply to the LED driver circuit 80 according to the first embodiment, the voltage rectified by the rectifier circuit 43 and smoothed by the smoothing circuit 44 fluctuates within the range of DC 11 V to DC 17 V when the capacity of the capacitor of the smoothing circuit 44 is suppressed to a certain capacity in order to prevent the inrush current from excessively increasing. In this case, since the voltage fluctuates above and below DC 13.8 V which is the forward voltage of the LED lamp 31, it is necessary to raise and lower this voltage.

When the AC 12 V internal power supply 42 is connected to the LED driver circuit 80, the input voltage level detector 45 detects that the voltage is lower than the reference supply voltage of 20 V, so that the change-over switch 47 is set to a connection state connecting with the lower terminal shown in FIG. 3 via the power connection switching unit 46.

At this time, the DC-DC converter circuit 40 functions as a step-up/down chopper circuit. The DC chopper controller 48 measures the current from the voltage across the resistor 56, and turns ON/OFF the transistor 54 based on the current, thereby controlling the current to the LED lamp 31. As a result, the voltage at node 51 fluctuates within the range of DC 11 V to DC 17 V. Correspondingly, the voltage at node 52 becomes a voltage obtained by adding DC 13.8 V which is the forward voltage of the LED lamp 31 to the voltage. For this reason, the DC 13.8 V which is a forward voltage is always applied to the LED lamp 31.

On the other hand, when the DC 24 V internal power supply 41 is connected as the internal power supply to the LED driver circuit 80 according to the first embodiment, the input voltage level detector 45 detects that the voltage is higher than the reference supply voltage of 20 V, so that the change-over switch 47 is set to a connection state connecting with the upper terminal, which is a connection state opposite to the connection state shown in FIG. 3, via the power connection switching unit 46.

At this time, the DC-DC converter circuit 40 functions as a step-down chopper circuit. The DC chopper controller 48 measures the current from the voltage across the resistor 56, and turns ON/OFF the transistor 54 based on the current, thereby controlling the current from the LED lamp 31. With this, DC 13.8 V which is a forward voltage is always applied to the LED lamp 31.

As described above, in the LED driver circuit 80 according to the first embodiment, either the step-up/down mode or the step-down mode is automatically selected corresponding to the internal power supply to be connected. Therefore, when the LED lamp 31 is used as a collimator lamp, even when the LED driver circuit 80 is connected to any one of the plurality of internal power supplies 41 and 42 different in voltage, it is possible to light the LED lamp 31 properly and safely.

In the LED driver circuit 80 according to the first embodiment, a plurality of types of internal power supplies different in voltage operates preferably when the internal power supply has a higher voltage than the forward voltage of the LED lamp 31 and the internal power supply has a voltage lower than the forward voltage of the LED lamp 31. In this case, each internal power supply is not required to be an AC (alternating current) power supply and a DC (direct current) power supply. In cases where an AC power supply is not used, it is possible to omit the rectifier circuit 43 and the smoothing circuit 44 described above.

In cases where an AC power supply is not used as each internal power supply and only a DC power supply is used, a step-up chopper circuit may be used instead of the step-up/down chopper circuit. That is, in such a case, as the DC-DC converter circuit 40, a DC-DC converter circuit having a function of a step-up chopper circuit and a function of a step-down chopper circuit may be used.

Figure 4:
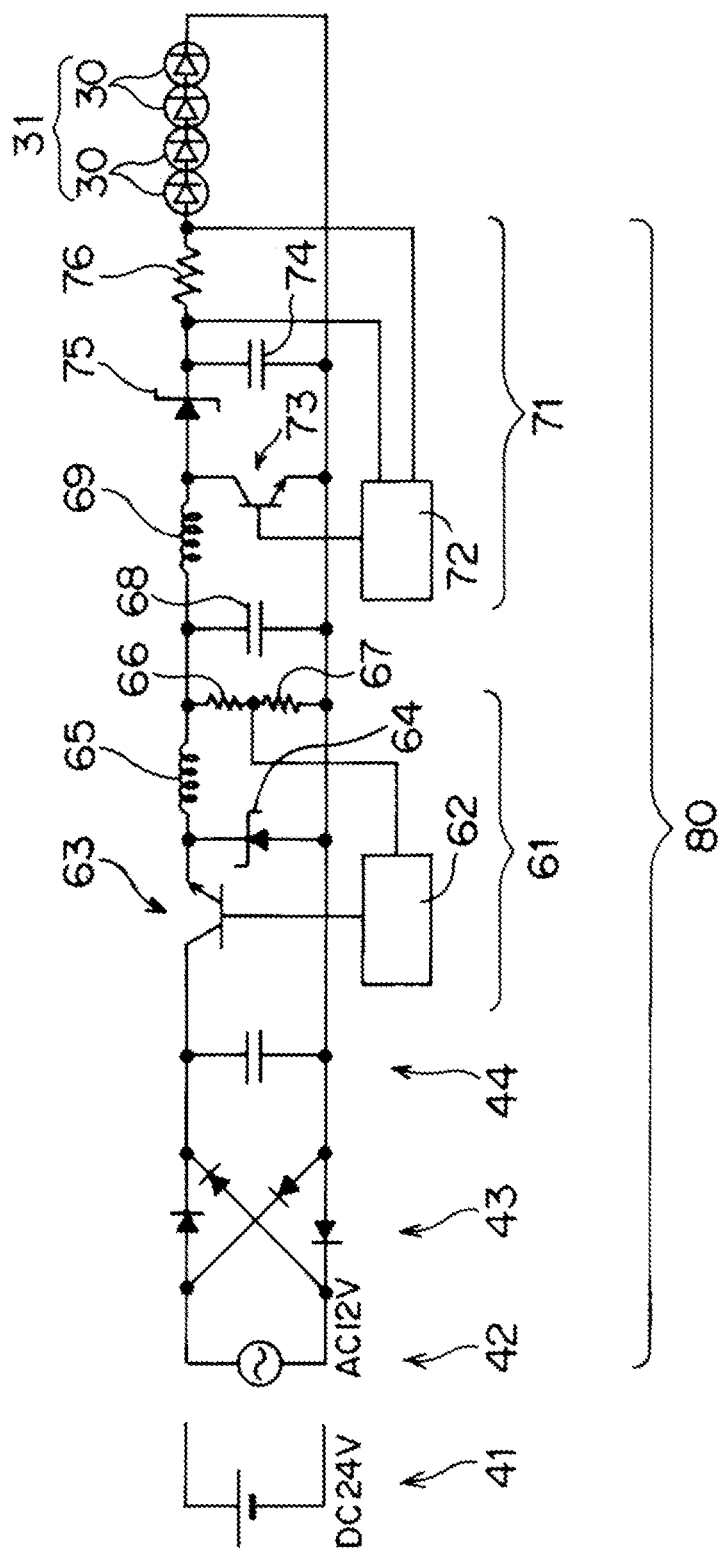
FIG. 4 is a circuit diagram of an LED driver circuit 80 according to a second embodiment of the present invention.

Next, another embodiment of the present invention will be described. FIG. 4 is a circuit diagram of an LED driver circuit 80 according to a second embodiment of the present invention.

Similar to the first embodiment, this LED driver circuit 80 is for supplying a forward voltage of each LED 30 to the LED lamp 31 by selectively connecting the DC 24 V internal power supply 41 and the AC 12V internal power supply 42 produced by the first transformer 21, the second transformer 22, and the AC/DC converter 23 shown in FIG. 5 to the LED lamp 31 composed of four LEDs 30 connected in series. Note that the forward voltage of the LED lamp 31 composed of four LEDs 30 is DC 13.8 V in the same manner as in the first embodiment.

The LED driver circuit 80 according to the second embodiment is provided with a rectifier circuit 43 having four diodes, a smoothing circuit 44 having a capacitor, a step-down circuit 61, and a step-up circuit 71.

[49] The step-down circuit 61 constitutes a voltage control type step-down chopper circuit, and is provided with a transistor 63, a Schottky barrier diode 64, a pair of resistors 66 and 67, a capacitor 68, and a step-down chopper controller 62. The step-down chopper controller 62 measures the voltage at a position between the pair of resistors 66 and 67 and executes the step-down action by turning the transistor 63 ON/OFF based on the voltage.

On the other hand, the step-up circuit 71 constitutes a current control type step-up chopper circuit, and includes a coil 69, a transistor 73, a Schottky barrier diode 75, a capacitor 74, a resistor 76, and a step-up chopper controller 72. The step-up chopper controller 72 measures the current from the voltage across the resistor 76 and executes the step-up action by turning the transistor 73 ON/OFF based on the current.

In the LED driver circuit 80 according to the second embodiment, in cases where the AC 12 V internal power supply 42 is connected as the internal power supply, except that it is rectified by the rectifier circuit 43 and smoothed by the smoothing circuit 44, the same operation will be executed even when the DC 24 V internal power supply 41 is connected and even when the AC 12 V internal power supply 41 is connected.

That is, when the internal power supply 41, 42 is connected to the LED driver circuit 80 according to the second embodiment, first, the voltage after passing through the smoothing circuit 44 by the step-down circuit 61 is stepped down to a voltage lower than the forward voltage of the LED lamp 31, for example, about 8 V. Next, by the step-up circuit 71, the voltage after step-down is boosted to 13.8 V which is the forward voltage of the LED lamp 31.

As described above, in the LED driver circuit 80 according to the second embodiment, the voltage of the internal power supply to be connected is stepped down to the forward voltage of the LED lamp 31 and then boosted to the forward voltage. Therefore, in the case of using the LED lamp 31 as a collimator lamp, even when the LED driver circuit 80 is connected to any one of the plurality of internal power supplies 41 and 42 different in voltage, it is possible to light the LED lamp 31 properly and safely.

In the LED driver circuit 80 according to the second embodiment, at least one of the plurality of types of internal power supplies different in voltage works well when the internal power supply is higher in voltage than the forward voltage of the LED lamp 31. In this case, each internal power supply is not required to be an AC (alternating current) power supply and a DC (direct current) power supply. In cases where an AC power supply is not used, it is possible to omit the rectifier circuit 43 and the smoothing circuit 44 described above.

In each of the first and second embodiments described above, the LED lamp 31 using four LEDs 30 has been described. However, the number of the LEDs 30 is not limited to four. Further, the LED lamp 31 may be composed of a single LED 30.

DESCRIPTION OF REFERENCE SYMBOLS

12: X-ray tube
13: collimator
14: X-ray detector
30: LED
31: LED lamp
33: collimator leaf
40: DC-DC converter circuit
41: internal power supply
42: internal power supply
43: rectifier circuit
44: smoothing circuit
45: input voltage level detector
46: power connection switching unit
47: change-over switch 48: DC chopper controller
61: step-down circuit
62: step-down chopper controller
71: step-up circuit
72: step-up chopper controller
80: LED driver circuit

The invention claimed is:

1. An X-ray imaging apparatus comprising:
    an X-ray tube;
    an X-ray detector configured to detect an X-ray irradiated from the X-ray tube and passed through a subject;
    a collimator equipped with a plurality of collimator leaves for changing an X-ray radiation field irradiated from the X-ray tube toward the subject and a collimator lamp for making the X-ray radiation field to be adjusted by the collimator leaves visible, wherein the collimator lamp comprises an LED lamp; and
    a plurality of types of internal power supplies different in voltage from each other; and
    an LED driver circuit connected to the LED lamp, the LED driver circuit is configured to connect to each of the internal power supplies and configured to convert a voltage of each of the internal power supplies as a connected internal power supply to a forward voltage of the LED lamp to thereby light the LED lamp.

2. The X-ray imaging apparatus as recited in claim 1, wherein
    the LED driver circuit includes:
    a DC-DC converter circuit capable of switching between a step-up/down mode or a step-up mode and a step-down mode according to a connection mode connecting any one of the plurality of types of internal power supplies with the DC-DC converter circuit;
    input voltage level detection means; and
    connection switching means configured to switch the connection mode connecting any one of the plurality of types of internal power supplies with the DC-DC converter circuit based on an input voltage detected by the input voltage level detection means.

3. The X-ray imaging apparatus as recited in claim 2, wherein
    the plurality of types of internal power supplies different in voltage include an internal power supply having a voltage higher than the forward voltage of the LED lamp and an internal power supply having a voltage lower than the forward voltage of the LED lamp.

4. The X-ray imaging apparatus as recited in claim 1, wherein
    the LED driver circuit includes:
    a step-down circuit for stepping down a voltage of any one of the plurality of types of internal power supplies to a voltage equal to or lower than the forward voltage of the LED lamp; and
    a step-up circuit for stepping up the voltage stepped down by the step-down circuit to the forward voltage of the LED lamp.

5. The X-ray imaging apparatus as recited in claim 4, wherein
    at least one of the plurality of types of internal power supplies different in voltage is an internal power supply having a voltage higher than the forward voltage of the LED lamp.

6. The X-ray imaging apparatus as recited in claim 1, wherein
    the plurality of types of internal power supplies different in voltage include an AC power supply having a voltage lower than the forward voltage of the LED lamp and a DC power supply having a voltage higher than the forward voltage of the LED lamp.

7. The X-ray imaging apparatus as recited in claim 1, wherein
    the LED driver circuit includes:
    input voltage level detection means; and
    connection switching means configured to switch an operation mode of the LED driver circuit based on an input voltage detected by the input voltage level detection means.

8. The X-ray imaging apparatus as recited in claim 1,
    wherein the plurality of types of internal power supplies comprise an AC power supply and a DC power supply,
    wherein the LED driver circuit is configured to connect to the AC power supply and convert the AC power supply to the forward voltage of the LED lamp, and
    wherein the LED driver circuit is configured to connect to the DC power supply and convert the DC power supply to the forward voltage of the LED lamp.

9. The X-ray imaging apparatus as recited in claim 8, wherein the DC power supply is a mechanical load power supply configured to drive a mechanical load of the X-ray imaging apparatus.

* * * * *